United States Patent
Yamashita et al.

(10) Patent No.: US 6,545,180 B1
(45) Date of Patent: Apr. 8, 2003

(54) PROCESS FOR THE PREPARATION OF SORBIC ACID

(75) Inventors: Akira Yamashita, Arai (JP); Mitsuhiro Kouno, Arai (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/555,097

(22) PCT Filed: Sep. 21, 1999

(86) PCT No.: PCT/JP99/05122

§ 371 (c)(1),
(2), (4) Date: May 24, 2000

(87) PCT Pub. No.: WO00/17144

PCT Pub. Date: Mar. 30, 2000

(30) Foreign Application Priority Data

Sep. 24, 1998 (JP) ........................................ 1998-288794

(51) Int. Cl.$^7$ .............................................. C07C 57/10
(52) U.S. Cl. ...................................................... 562/601
(58) Field of Search ......................................... 562/601

(56) References Cited

U.S. PATENT DOCUMENTS 3,845,118 A * 10/1974 Hey et al.
3,992,442 A * 11/1976 Kageyama et al.

FOREIGN PATENT DOCUMENTS

| JP | B1-4426646 | 11/1969 |
| JP | A54103821 | 8/1979 |

OTHER PUBLICATIONS

Derwent abstract of DE 1793441 A. Preparation of sorbic acid by reaction of ketene and crotonaldehyde (1972).*
Derwent abstract of JP 09227447 A. Preparation of sorbic acid used as a food preservative—comprises hydrolysing polyester obtained by lactonisation of crotonaldehyde and keten and isomerising (1997).*
Derwent abstract of JP 54103821. Recovering sorbic acid from aq. dilute soln. of sorbic acid—by subjecting polyester to decomposition with acid, recrystallizing sorbic acid from hot water, adjusting pH etc. (1979).*
Ault (1987). Techniques and Experiments for organic chemistry, pp 294–296.*

* cited by examiner

*Primary Examiner*—Ralph Gitomer
(74) *Attorney, Agent, or Firm*—Birch, Stewart, Kolasch & Birch, LLP

(57) ABSTRACT

The invented process for producing sorbic acid includes the step of decomposing a polyester at temperatures of 100° C. or less with hydrochloric acid, which polyester is obtained from ketene and crotonaldehyde. In the process, the reaction temperature after the initiation of a polyester decomposition reaction is controlled by adding a hydrochloric acid to a reaction mixture, which hydrochloric acid has a temperature lower than that of the reaction mixture, for example, a temperature of 50° C. or less. Such hydrochloric acid for reaction control may have a concentration of, for example, 23% by weight or more. This process can yield sorbic acid in a short time in a high yield and can highly efficiently produce sorbic acid.

2 Claims, No Drawings

PROCESS FOR THE PREPARATION OF SORBIC ACID

TECHNICAL FIELD

The present invention relates to a process for producing sorbic acid which is useful as, for example, food additives. Particularly, the invention relates to a process for producing sorbic acid by decomposing a polyester by action of hydrochloric acid, which polyester is obtained from ketene and crotonaldehyde.

BACKGROUND ART

As processes for the commercial production of sorbic acid, processes are known which include the step of decomposing a polyester with hydrochloric acid, which polyester is obtained by a reaction of ketene with crotonaldehyde. For example, Japanese Examined Patent Application Publication No. 44-26646 discloses a process for producing sorbic acid. The process includes the steps of reacting ketene with crotonaldehyde in the presence of a catalyst to yield a reaction mixture, heating the reaction mixture under reduced pressure to remove unreacted crotonaldehyde and by-products of the reaction by distillation to yield a polyester containing the catalyst, decomposing the polyester with hydrochloric acid to yield a reaction mixture, and cooling the reaction mixture to yield sorbic acid.

In the step of decomposing the polyester with hydrochloric acid to yield sorbic acid, the polyester should be preferably decomposed at somewhat high temperatures in a short time, from the viewpoint of a production efficiency. Separately, in the decomposition of the polyester with hydrochloric acid, the mixture must be heated in an initial stage but the heat may invite by-production of tar substances. Particularly, the by-production is enhanced at high temperatures. When the polyester is decomposed in a batch system, a large amount of heat is evolved after the initiation of the decomposition reaction. Such heat includes precipitation heat evolved through precipitation of formed sorbic acid. The reaction mixture must be aged at somewhat high temperatures even after the heat generation calms down. If the aging temperature is excessively high, side reactions increase, and if the aging temperature is excessively low, the decomposition rate or isomerization rate of the polyester decreases. In both cases, the yield of sorbic acid decreases. Accordingly, in the polyester decomposition step, the reaction temperatures, particularly the maximum temperature upon heat generation (hereinafter referred to as "peak temperature") and the reaction temperature in an aging stage after attaining the peak temperature must be delicately and precisely controlled.

Generally, the polyester decomposition reaction is performed using a reactor with a jacket. The reaction temperature is controlled by allowing steam to pass through the jacket in an early stage of the reaction, or by allowing a cooling water to pass through the jacket in a later stage after the reaction proceeds to some extent. However, if the reaction is performed at relatively high temperatures to complete the reaction in a short time, heat such as the precipitation heat of sorbic acid is convergently evolved just before attaining the peak temperature. The heat cannot be immediately removed according to the above techniques for heat removal, and the reaction temperatures (peak temperature and aging temperature) cannot be significantly precisely controlled.

The Japanese Examined Patent Application Publication No. 44-26646 discloses a process for producing sorbic acid. The process includes the steps of preparing a polyester from ketene and crotonaldehyde, and decomposing the polyester with hydrochloric acid having a concentration of 35% by weight or more at temperatures ranging from room temperature to around the boiling point of the hydrochloric acid used. Japanese Examined Patent Application Publication No.45-16445 discloses a process for producing sorbic acid. This process includes the steps of putting the polyester into relatively large amounts of hydrochloric acid, treating the polyester at temperatures ranging from room temperature to 80° C., removing hydrochloric acid from a reaction mixture containing precipitated sorbic acid and unreacted polyester, heating the mixture to high temperatures ranging from 110° C. to 250° C. to thereby recover the formed sorbic acid by distillation. Japanese Unexamined Patent Application Publication No. 9-227447 discloses a process for producing sorbic acid. The process includes the step of performing isomerization after the completion of heat generation in the hydrolysis of the polyester. The isomerization is performed at a temperature of 25° C. or higher, which temperature is 4° C. or more lower than the temperature at the time when heat generation completes. Japanese Unexamined Patent Application Publication No. 10-95745 discloses a process for producing sorbic acid, including the step of hydrolyzing the polyester with a mineral acid in the presence of a saturated fatty acid. However, these publications fail to describe how the reaction temperatures in decomposition of the polyester with hydrochloric acid should be controlled.

DISCLOSURE OF INVENTION

Accordingly, an object of the invention is to provide a process which is capable of yielding sorbic acid in a short time in a high yield and capable of producing sorbic acid with a high production efficiency.

Another object of the invention is to provide a process which is capable of easily and precisely controlling reaction temperatures in a polyester decomposition step and of stably providing a high-quality sorbic acid.

To achieve the above objects, the present inventors made intensive investigations on processes for controlling reaction temperatures in decomposition of a polyester with hydrochloric acid, which polyester is obtained by a reaction of ketene with crotonaldehyde. Consequently, the inventors found that the reaction temperatures can be easily controlled even at relatively high temperatures by adding a specific hydrochloric acid to a reaction mixture in a heat generation stage after the initiation of a reaction. The present invention has been accomplished based on these findings.

Specifically, the invention provides a process for producing sorbic acid. The process includes the step of decomposing a polyester at temperatures of 100° C. or less by action of hydrochloric acid, which polyester is obtained from ketene and crotonaldehyde. In the process, the reaction temperature after the initiation of a polyester decomposition reaction is controlled by adding a hydrochloric acid to a reaction mixture, which hydrochloric acid has a temperature lower than that of the reaction mixture.

BEST MODE FOR CARRYING OUT THE INVENTION

According to the invention, a polyester obtained from ketene and crotonaldehyde is decomposed with hydrochloric acid to yield sorbic acid. The polyester is generally shown by the following formula (1):

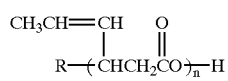

In the above formula, R is an acetoxy group or a hydroxyl group, and n denotes an integer of 2 or more (e.g., about 3 to 40).

The polyester can be obtained by conventional or known processes. For example, the polyester is obtained by reacting ketene with crotonaldehyde in the presence of a catalyst and in the absence of or in the presence of an inert solvent. Such catalysts include, but are not limited to, simple substances or compounds of manganese, cobalt, nickel, zinc, cadmium, and other transition metals; and pyridine, picoline, and other nitrogen-containing basic compounds. Examples of the compounds of the transition metals are oxides; salts of acetic acid, salts of isobutyric acid, salts of isovaleric acid, and salts of other organic acids; salts of sulfuric acid, salts of nitric acid, and salts of other inorganic acids; chlorides and other halides; acetylacetone complex salts, and other complex salts and complexes. Each of these catalysts can be used alone or in combination. The amount of the catalyst differs according to the type of the catalyst, but is generally about 0.1 to 10% by weight relative to the weight of ketene.

The reaction of ketene with crotonaldehyde is performed at a temperature of, for example, about 20° C. to 100° C., and preferably about 25° C. to 80° C.

A reaction mixture containing a polyester obtained through the reaction of ketene with crotonaldehyde is usually distilled to remove unreacted crotonaldehyde and low boiling impurities, and is then subjected to a decomposition reaction with hydrochloric acid.

The decomposition reaction of polyester is generally commenced by heating a mixture containing the polyester and hydrochloric acid. The hydrochloric acid for use at the beginning of the reaction can be appropriately selected according to the reaction rate or easiness of the hydrochloric acid to be handled, and generally has a concentration of 23% or more (e.g., about 23 to 36% by weight) and preferably about 33 to 35% by weight. The amount of hydrochloric acid for use at the beginning of the reaction is, for example in terms of hydrogen chloride, about 10 to 160 parts by weight, preferably about 15 to 100 parts by weight, more preferably about 18 to 50 parts by weight, and typically about 20 to 40 parts by weight, relative to 100 parts by weight of the polyester.

After the initiation of the reaction, sorbic acid is formed and the formed sorbic acid begins to precipitate, and with this, heat such as precipitation heat of sorbic acid is evolved. A reaction system must be therefore cooled. According to the invention, reaction temperatures after the initiation of polyester decomposition reaction are controlled by adding a hydrochloric acid to a reaction mixture, which hydrochloric acid has a temperature lower than a reaction mixture.

Such cooling hydrochloric acid for use in control of the reaction temperatures generally has a concentration of 23% by weight or more (e.g., about 23 to 36% by weight) and preferably about 24 to 30% by weight. An excessively low concentration of the cooling hydrochloric acid may decrease the yield of sorbic acid, and in contrast, an excessively high concentration may be disadvantageous in handling property. The amount of the cooling hydrochloric acid varies according to, for example, the target reaction temperature and the temperature of the cooling hydrochloric acid, but is generally about 100 to 500 parts by weight, preferably about 150 to 400 parts by weight, and more preferably about 200 to 300 parts by weight, relative to 100 parts by weight of the polyester. The temperature of the cooling hydrochloric acid has only to be lower than that of the reaction mixture, and is generally 50° C., or less (e.g., about 0° C. to 50° C.), and preferably about 15° C. to 45° C. Hydrochloric acid at room temperature is frequently used, as such hydrochloric acid can be easily handled. As the cooling hydrochloric acid, a recovered hydrochloric acid can be commercially advantageously employed, as well as a fresh hydrochloric acid.

To the reaction mixture, the cooling hydrochloric acid may be added all at once or in several installments, or may be continuously added for a predetermined time. The reaction temperatures may be controlled by the addition of the cooling hydrochloric acid to the reaction mixture alone, or by a combination of the addition and another temperature control means (heat removing means) such as allowance of a cooling water to pass through a jacket or coil provided in the reactor.

In the polyester decomposition step, the reaction temperatures cannot be precisely controlled by, for example, early stopping of heating or allowance of a cooling water to pass through the jacket or the like, without the addition of a cooling hydrochloric acid. Particularly, when the target reaction temperatures are relatively high, the heat is abruptly evolved and the peak temperature and the reaction temperature in aging stage after heat generation calms down cannot be significantly controlled. Thus, sorbic acid having a desirable quality cannot be stably obtained. In contrast, according to the invention, the cooling hydrochloric acid is directly added to the reaction mixture and the heat can be rapidly removed. The reaction temperatures can be precisely controlled even when the target reaction temperatures are relatively high. Accordingly, a high-quality sorbic acid can be stably provided with a high production efficiency.

The reaction temperature of the polyester decomposition reaction is 100° C. or less (e.g., about 50° C. to 100° C.), preferably about 55° C. to 96° C., and more preferably about 60° C. to 95° C. From the viewpoint of reaction efficiency, the peak temperature should preferably have a lower limit of about 80° C. A reaction temperature exceeding 100° C. may markedly increase by-production of tar. In contrast, an extremely low reaction temperature will prolong a reaction time to thereby decrease the production efficiency of sorbic acid. The aging temperature after the heat generation calms down ranges, for example, from 60° C. to the peak temperature, and preferably from 75° C. to the peak temperature. An aging at temperatures within this range can yield sorbic acid in a high yield and can complete the reaction in a short aging time of, for example, about 30 minutes to 2 hours, and preferably about 40 minutes to 1.5 hours.

According to an preferred embodiment of the invention, the peak temperature in the polyester decomposition step is controlled in a range from 87° C. to 96° C., and typically from 90° C. to 95° C., and the aging temperature in the polyester decomposition step is controlled in a range from 75° C. to the peak temperature.

Sorbic acid can be obtained by subjecting a reaction mixture obtained through the polyester decomposition to a conventional separation and purification means such as crystallization, filtration, centrifugal separation, treatment with active carbon, distillation, or recrystallization.

The product sorbic acid and its salts can be used as preservatives for foods such as fish pastes, butters, cheeses, bean pastes, and jams.

The invention controls heat generation after the initiation of the polyester decomposition reaction by directly adding the cooling hydrochloric acid to the reaction mixture and can highly efficiently remove the heat. Even when the target reaction temperatures are relatively high, the reaction temperatures can be easily and precisely controlled to yield sorbic acid in a short time in a high yield. A high-quality sorbic acid can be stably provided.

The present invention will now be illustrated in further detail with reference to an inventive example and several comparative examples below, which are not intended to limit the scope of the invention. All "parts" are by weight unless otherwise specified.

EXAMPLE 1

To 600 parts of crotonaldehyde, 2 parts of zinc isobutyrate was added as a catalyst, and 170 parts of a ketene gas was introduced at a temperature of 30° C. to 40° C. to perform a reaction. After the completion of reaction, excess crotonaldehyde was removed by distillation under reduced pressure to yield a highly viscous polyester. The yield of the polyester was 77% on the basis of ketene.

In a glass reactor with a jacket and a stirrer, 100 parts of the above-prepared polyester and 70 parts of a concentrated hydrochloric acid having a concentration of 34% by weight were placed. The reactor was heated by allowing steam to pass through the jacket, and the heating by steam was stopped at the time when the temperature in the reactor (reaction temperature) reached around 80° C. Thereafter, the reaction temperature continuously increased predominantly due to precipitation heat of sorbic acid. At the time when the reaction temperature reached around 85° C., a cooling water was allowed to pass through the jacket, and subsequently 250 parts of a cooling hydrochloric acid having a concentration of 25% by weight was placed into the reactor. The reaction temperature attained maximum at about 88° C. and then began to decrease gradually. At the point when the reaction temperature began to decrease, the cooling water was stopped. The reaction temperature decreased to 80° C. one hour after the time when the reaction temperature attained maximum (peak). A slurry containing sorbic acid was thus obtained, and the slurry was separated to a solid and a liquid by suction filtration, and the solid was dried to yield 90 parts of sorbic acid.

COMPARATIVE EXAMPLE 1

A polyester was prepared in the same manner as in Example 1. In a glass reactor with a jacket and a stirrer, 100 parts of the above-prepared polyester and 70 parts of a concentrated hydrochloric acid having a concentration of 34% by weight were placed. The reactor was heated by allowing steam to pass through the jacket, and the heating by steam was stopped at the time when a reaction temperature reached around 80° C. Thereafter, the reaction temperature continuously increased predominantly due to precipitation heat of sorbic acid. At the time when the reaction temperature reached around 85° C., a cooling water was allowed to pass through the jacket. As a result, the reaction temperature continuously increased even after the temperature exceeded 90° C., attained maximum at about 93° C. and then began to decrease. The cooling water was stopped at the time when the reaction temperature reached 90° C., the reaction temperature then rapidly decreased, and reached 70° C. one hour after the time when the reaction temperature attained maximum (peak). A slurry containing sorbic acid was thus obtained, and the slurry was separated to a solid and a liquid by suction filtration, and the solid was dried to yield 85 parts of sorbic acid.

COMPARATIVE EXAMPLE 2

A polyester was prepared in the same manner as in Example 1. In a glass reactor with a jacket and a stirrer, 100 parts of the above-prepared polyester and 70 parts of a concentrated hydrochloric acid having a concentration of 34% by weight were placed. The reactor was heated by allowing steam to pass through the jacket, and the heating by steam was stopped at the time when a reaction temperature reached around 75° C. Thereafter, the reaction temperature gradually increased. At the time when the reaction temperature reached around 85° C., a cooling water was allowed to pass through the jacket. The reaction temperature continuously increased even the temperature exceeded 90° C., attained maximum at about 95° C. and then began to decrease. The cooling water was stopped at the time when the reaction temperature began to decrease, and the reaction temperature then gradually decreased, and reached 85° C. one hour after the time when the reaction temperature attained maximum (peak). A slurry containing sorbic acid was thus obtained, and the slurry was separated to a solid and a liquid by suction filtration, and the solid was dried to yield 85 parts of sorbic acid.

What is claimed is:

1. A batch process for producing sorbic acid comprising the step of decomposing a polyester at temperatures of 100° C. or less by action of hydrochloric acid, said polyester being obtained from ketene and crotonaldehyde, wherein a peak temperature in the polyester decomposition step is controlled in a range of 80° C. to 100° C. and an aging procedure is performed at a temperature in a range from 75° C. to the peak temperature for 30 minutes to 2 hours after the reaction temperature reaches the peak temperature by adding a hydrochloric acid having a temperature lower than that of the polyester decomposition reaction mixture, said hydrochloric acid having a concentration of 24 to 30% by weight being added in an amount of 100 to 500 parts by weight relative to 100 parts by weight of the polyester to the reaction mixture after the initiation of the polyester decomposition reaction.

2. A batch process for producing sorbic acid comprising the steps of (a) reacting ketene and crotonaldehyde to form a polyester, (b) decomposing said polyester at temperatures of 100° C. or less by a first action of hydrochloric acid at a peak temperature controlled in a range of 80° C. to 100° C., and (c) performing an aging procedure at a temperature in a range from 75° C. to said peak temperature for 30 minutes to 2 hours after the reaction temperature reaches the peak temperature, wherein said aging procedure is performed by a second addition of hydrochloric acid, having a concentration of 24–30% by weight and having a temperature lower than that of the polyester decomposition reaction mixture, in an amount of 100 to 500 parts by weight relative to 100 parts by weight of the polyester to the reaction mixture after the initiation of the polyester decomposition reaction.

* * * * *